United States Patent
Beckett et al.

(10) Patent No.: US 7,640,481 B2
(45) Date of Patent: Dec. 29, 2009

(54) INTEGRATED CIRCUIT HAVING MULTIPLE MODES OF OPERATION

(75) Inventors: Richard C. Beckett, Phoenix, AZ (US); Deif N. Atallah, Chandler, AZ (US)

(73) Assignee: Intel Corporation, Santa Clara, CA (US)

( * ) Notice: Subject to any disclaimer, the term of this patent is extended or adjusted under 35 U.S.C. 154(b) by 529 days.

(21) Appl. No.: 11/389,340

(22) Filed: Mar. 23, 2006

(65) Prior Publication Data

US 2006/0168367 A1     Jul. 27, 2006

Related U.S. Application Data

(63) Continuation of application No. 10/301,028, filed on Nov. 20, 2002, now Pat. No. 7,206,989.

(51) Int. Cl.
*G11C 29/00* (2006.01)
*G06F 3/00* (2006.01)

(52) U.S. Cl. .......................... 714/766; 710/11
(58) Field of Classification Search ................ 714/766; 710/11
See application file for complete search history.

(56) References Cited

U.S. PATENT DOCUMENTS

| | | | |
|---|---|---|---|
| 5,257,391 A | 10/1993 | DuLac et al. | |
| 5,345,565 A | 9/1994 | Jibbe et al. | |
| 5,509,121 A | 4/1996 | Nakata et al. | |
| 5,841,985 A | 11/1998 | Jie et al. | |
| 5,884,044 A | 3/1999 | Marsanne et al. | |
| 5,920,893 A | 7/1999 | Nakayama et al. | |
| 5,922,062 A | 7/1999 | Evoy | |
| 5,946,634 A | 8/1999 | Korpela | |
| 6,038,400 A | 3/2000 | Bell et al. | |
| 6,072,803 A | 6/2000 | Allmond et al. | |
| 6,115,771 A | 9/2000 | Born | |
| 6,115,797 A | 9/2000 | Kanda et al. | |

(Continued)

FOREIGN PATENT DOCUMENTS

DE     19616753     12/1996

(Continued)

OTHER PUBLICATIONS

DSLWebserver.com, Diagram:Single Computer Using NAT + Crossover Cable, May 29, 2001.

(Continued)

*Primary Examiner*—James C Kerveros (57) ABSTRACT

A method according to one embodiment may include operating an integrated circuit in a selected mode of operation. The integrated circuit may include first circuitry and second circuitry. The first circuitry may be capable of performing at least one operation including, at least in part, generating check data based at least in part upon other data, regenerating the other data based at least in part upon the check data, and/or determining locations of the check data and the other data in storage. The second circuitry may be capable of controlling, at least in part, at least one interface to transmit from and/or receive at the integrated circuit the check data and/or the other data. Depending at least in part upon the selected mode of operation, the first circuitry may be either enabled to perform or disabled from performing the at least one operation.

26 Claims, 5 Drawing Sheets

U.S. PATENT DOCUMENTS

| | | | |
|---|---|---|---|
| 6,189,052 | B1 | 2/2001 | Nilsson et al. |
| 6,240,482 | B1 * | 5/2001 | Gates et al. ............... 710/306 |
| 6,246,271 | B1 | 6/2001 | Takada et al. |
| 6,246,671 | B1 | 6/2001 | Glass, III et al. |
| 6,253,268 | B1 | 6/2001 | Bjorkengren et al. |
| 6,334,160 | B1 | 12/2001 | Emmert et al. |
| 6,438,678 | B1 | 8/2002 | Cashman et al. |
| 6,504,851 | B1 | 1/2003 | Abler et al. |
| 6,633,933 | B1 | 10/2003 | Smith et al. |
| 6,640,278 | B1 | 10/2003 | Nolan et al. |
| 6,643,654 | B1 | 11/2003 | Patel et al. |
| 6,690,655 | B1 | 2/2004 | Miner et al. |
| 6,721,854 | B1 | 4/2004 | Asano et al. |
| 6,721,872 | B1 | 4/2004 | Dunlop et al. |
| 6,728,795 | B1 * | 4/2004 | Farazmandnia et al. ....... 710/22 |
| 6,742,060 | B2 | 5/2004 | Poisner et al. |
| 6,748,488 | B2 | 6/2004 | Byrd |
| 6,779,063 | B2 | 8/2004 | Yamamoto |
| 6,871,244 | B1 | 3/2005 | Cahill et al. |
| 6,928,521 | B1 * | 8/2005 | Burton et al. ............... 711/144 |
| 7,073,022 | B2 | 7/2006 | El-Batal et al. |
| 7,080,190 | B2 * | 7/2006 | Weber ..................... 710/315 |
| 7,107,385 | B2 | 9/2006 | Rajan et al. |
| 2003/0074515 | A1 | 4/2003 | Resnick |
| 2003/0093598 | A1 | 5/2003 | Park |
| 2003/0219003 | A1 | 11/2003 | Parekh |
| 2003/0219033 | A1 | 11/2003 | Silvester |
| 2003/0221061 | A1 | 11/2003 | El-Batal et al. |
| 2003/0225724 | A1 | 12/2003 | Weber |
| 2003/0229739 | A1 | 12/2003 | Brewer et al. |
| 2003/0229748 | A1 | 12/2003 | Brewer et al. |
| 2003/0237022 | A1 | 12/2003 | Thayer |
| 2004/0015762 | A1 | 1/2004 | Klotz et al. |
| 2004/0024858 | A1 | 2/2004 | Garcelon et al. |
| 2004/0030822 | A1 | 2/2004 | Rajan et al. |
| 2004/0064612 | A1 * | 4/2004 | Pinto et al. ............... 710/105 |
| 2004/0081179 | A1 | 4/2004 | Gregorcyk, Jr. |
| 2004/0098518 | A1 | 5/2004 | Beckett et al. |
| 2004/0098530 | A1 | 5/2004 | Earl et al. |
| 2004/0098645 | A1 | 5/2004 | Beckett et al. |
| 2004/0204029 | A1 | 10/2004 | Parry |
| 2005/0015532 | A1 | 1/2005 | Beckett et al. |
| 2005/0149793 | A1 | 7/2005 | Beckett et al. |

FOREIGN PATENT DOCUMENTS

| | | |
|---|---|---|
| DE | 10056198 | 2/2002 |
| EP | 0508604 | 11/1992 |
| WO | WO 01/25942 A1 | 4/2001 |
| WO | PCT/US03/34803 | 3/2004 |
| WO | PCT/US03/34368 | 6/2004 |
| WO | WO 2004046913 A2 | 6/2004 |
| WO | PCT/US2004/012021 | 2/2005 |

OTHER PUBLICATIONS

DSLWebserver.com, Diagram:Two Computer Crossover Cable Network, Jun. 10, 2001.

SearchNetworking.com, Definitions for Crossover Cable, Sep. 16, 2002.

Intel Corporation product brief, 2 pages.

Intel Corporation, Intel Network Infrastructure Processors, Extending Intelligence in the Network.

Benner, Alan, "Fibre Channel Gigabit Comm. and I/O for Computer Networks," McGraw Hill 1996, Chapters 6, 7, 8, 12 and 17.

Intel Corp., AAU Support Library for the Intel 80310 I/O Processor Chipset and 80321 I/O Processor, Reference Manual, Apr. 2002.

Intel Corp., Intel XScale Microarchitecture, Technical Summary, 2002.

Postel, J., et al., Internet Control Message Protocol, DARPA Internet Program Protocol Specification, Sep. 1981, 19 pages.

Internet Protocol, DARPA Internet Program Protocol Specification, Information Sciences Institute, Univ. of Sourthern CA, Sep. 1981, 45 pages.

Elliot, R., et al., Serial Attached SCSI, Proposed Serial Attached SCSI working draft, Apr. 25, 2002.

Deyring, K.P. et al., Serial ATA: High Speed Specialized AT Attachment, Revision 1.0, Aug. 29, 2001.

Intel Corporation, Intel XScale Core, Developer's Manual, Dec. 2000.

http://www.promise.com/support/download/download2.sub.—eng. asp?category=a-ll&os=100&productID=18.

X-bit Labs article—"VIA KT266: Final Verdict. MSI K7T266 Pro Mainboard" found at http://www.xbitlabs.com/articles/mainboards/display/msi-k7t266-p-ro.html—Dated May 10, 2001.

International Preliminary Report on Patentability for Patent Application No. PCT/US2004/012021, mailed Dec. 8, 2005, 6 Pages.

Ultra 100 User Manual found at : .quadrature..quadrature. http://www.promise.com/support/download/download2-.sub.—eng. asp?category=all&os=100&productID=18. quadrature..quadrature. Dat-ed Nov. 21, 2000.

Office Action mailed on Jul. 27, 2006 regarding U.S. Appl. No. 10/301,027, filed Nov. 20, 2002.

Office Action mailed on Jul. 27, 2006 regarding U.S. Appl. No. 11/036,418, filed Jan. 14, 2005.

* cited by examiner

INTEGRATED CIRCUIT HAVING MULTIPLE MODES OF OPERATION

CROSS-REFERENCE TO RELATED APPLICATION

This is a continuation of application Ser. No. 10/301,028, entitled "Integrated Circuit Having Multiple Modes Of Operation," filed Nov. 20, 2002, now U.S. Pat. No. 7,206,989. The subject application is related to co-pending U.S. patent application Ser. No. 10/301,027, entitled "Integrated Circuit Having Multiple Modes Of Operation," filed Nov. 20, 2002, now U.S. Pat. No. 7,543,085. The subject application is also related to co-pending U.S. patent application Ser. No. 11/036,418, entitled "Integrated Circuit Having Multiple Modes Of Operation," filed Jan. 14, 2005, now U.S. Pat. No. 7,421,517. The subject application is also related to co-pending U.S. patent application Ser. No. 10/442,705, entitled "Integrated Circuit Capable of Communicating Using Different Communication Protocols," filed May 20, 2003, now U.S. Pat. No. 7,093,033. Each of these related applications is assigned to the Assignee of the subject application.

FIELD

This disclosure relates to an integrated circuit having multiple modes of operation.

BACKGROUND

In one conventional data storage arrangement, a computer node includes a host bus adapter (HBA). The HBA communicates with host devices via the host bus using a host bus protocol associated with the host bus. The HBA also communicates with a data storage system via one or more communication links using a communication protocol associated with the one or more links. If the data storage system includes a redundant array of independent disks (RAID), the HBA typically also carries out RAID-related operations (e.g., operations involved in implementing the RAID).

The HBA includes a plurality of integrated circuit chips that the HBA uses to carry out communications between the HBA and the host processor, communications between the HBA and the data storage system, and the operations involved in implementing the RAID. Typically, these integrated circuit chips limit the communication capabilities of the HBA such the HBA is capable of using only a single predetermined host bus protocol and only a single predetermined communication protocol.

BRIEF DESCRIPTION OF THE DRAWINGS

Features and advantages of embodiments of the claimed subject matter will become apparent as the following Detailed Description proceeds, and upon reference to the Drawings, wherein like numerals depict like parts, and in which:

Although the following Detailed Description will proceed with reference being made to illustrative embodiments, many alternatives, modifications, and variations thereof will be apparent to those skilled in the art. Accordingly, it is intended that the claimed subject matter be viewed broadly, and be defined only as set forth in the accompanying claims.

DETAILED DESCRIPTION

Figure 1:
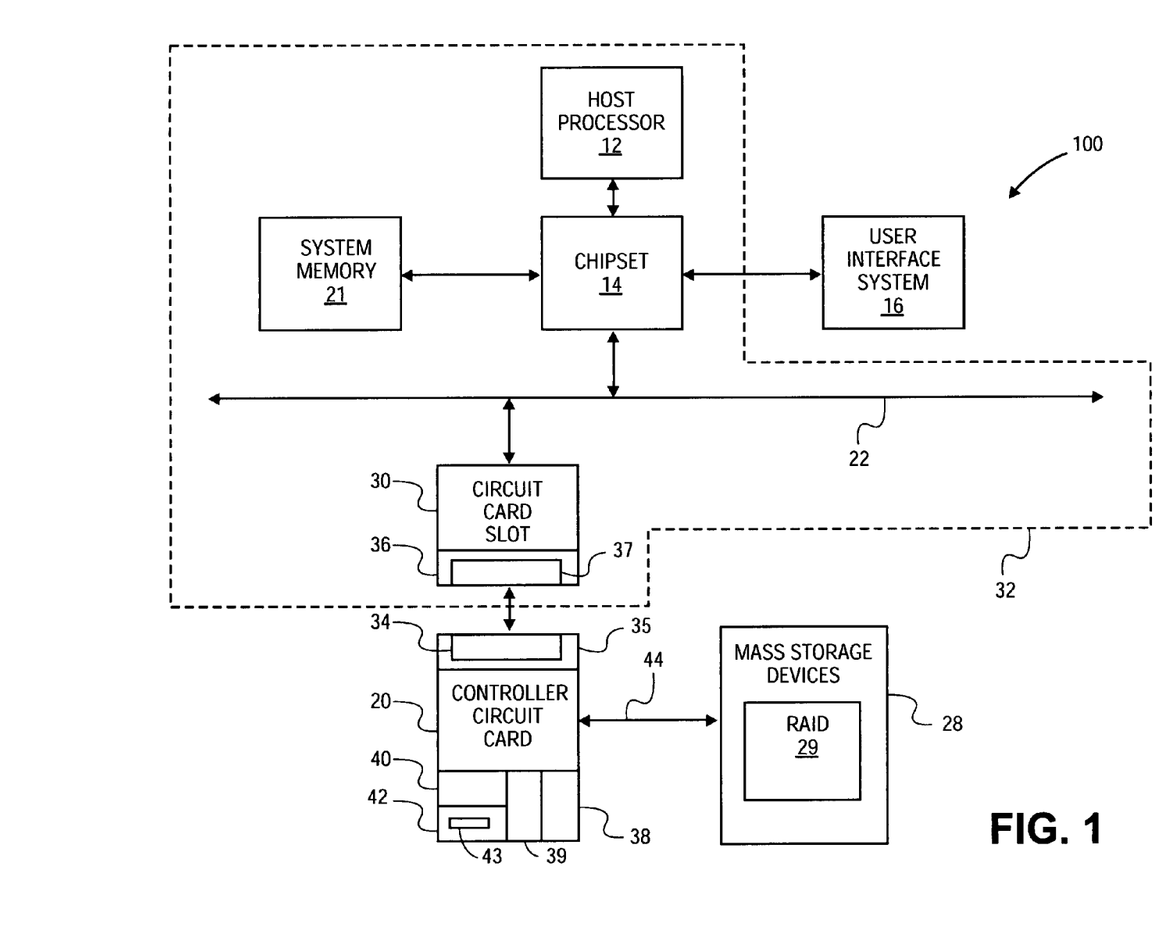
FIG. 1 is a diagram illustrating a system embodiment.

FIG. 1 illustrates a system embodiment 100 of the claimed subject matter. System 100 may include a host processor 12 coupled to a chipset 14. Host processor 12 may comprise, for example, an Intel® Pentium® IV microprocessor that is commercially available from the Assignee of the subject application. Of course, alternatively, host processor 12 may comprise another type of microprocessor, such as, for example, a microprocessor that is manufactured and/or commercially available from a source other than the Assignee of the subject application, without departing from this embodiment.

Chipset 14 may comprise a host bridge/hub system that may couple host processor 12, a system memory 21 and a user interface system 16 to each other and to a bus system 22. Chipset 14 may also include an I/O bridge/hub system (not shown) that may couple the host bridge/bus system to bus 22. Chipset 14 may comprise integrated circuit chips, such as those selected from integrated circuit chipsets commercially available from the assignee of the subject application (e.g., graphics memory and I/O controller hub chipsets), although other integrated circuit chips may also, or alternatively be used, without departing from this embodiment. User interface system 16 may comprise, e.g., a keyboard, pointing device, and display system that may permit a human user to input commands to, and monitor the operation of, system 100.

Bus 22 may comprise a bus that complies with the Peripheral Component Interconnect (PCI) Express™ Base Specification Revision 1.0, published Jul. 22, 2002, available from the PCI Special Interest Group, Portland, Oreg., U.S.A. (hereinafter referred to as a "PCI Express™ bus"). Alternatively, bus 22 instead may comprise a bus that complies with the PCI-X Specification Rev. 1.0a, Jul. 24, 2000, available from the aforesaid PCI Special Interest Group, Portland, Oreg., U.S.A. (hereinafter referred to as a "PCI-X-bus"). Also alternatively, bus 22 may comprise other types and configurations of bus systems, without departing from this embodiment.

Controller card 20 may be coupled to and control the operation of mass storage 28. In this embodiment, mass storage 28 may comprise, e.g., one or more redundant arrays of inexpensive disks (RAID) 29. The RAID level that may be implemented by RAID 29 may be 0, 1, or greater than 1.

Processor 12, system memory 21, chipset 14, bus 22, and circuit card slot 30 may be comprised in a single circuit board, such as, for example, a system motherboard 32. Mass storage 28 may be comprised in one or more respective enclosures that may be separate from the enclosure in which the motherboard 32 and the components comprised in the motherboard 32 are enclosed.

Card 20 may be coupled to mass storage 28 via one or more network communication links 44. As is discussed in below, depending at least in part upon the operating mode of an integrated circuit 40 that may be comprised in card 20, card 20 may exchange data and/or commands with mass storage 28, via links 44, using one or more of a variety of different communication protocols, e.g., Fibre Channel (FC), Serial Advanced Technology Attachment (S-ATA), and/or Serial Attached Small Computer Systems Interface (SAS) protocol. Of course, alternatively, I/O controller card 20 may exchange data and/or commands with mass storage 28 using other and/or additional communication protocols, without departing from this embodiment.

In accordance with this embodiment, if a FC protocol is used by controller card 20 to exchange data and/or commands with mass storage 28, it may comply or be compatible with the interface/protocol described in ANSI Standard Fibre Channel (FC) Physical and Signaling Interface-3 X3.303: 1998 Specification. Alternatively, if a S-ATA protocol is used by controller card 20 to exchange data and/or commands with mass storage 28, it may comply or be compatible with the protocol described in "Serial ATA: High Speed Serialized AT Attachment," Revision 1.0, published on Aug. 29, 2001 by the Serial ATA Working Group. Further alternatively, if a SAS protocol is used by controller card 20 to exchange data and/or commands with mass storage 28, it may comply or be compatible with the protocol described in "Information Technology—Serial Attached SCSI (SAS)," Working Draft American National Standard of International Committee For Information Technology Standards (INCITS) T10 Technical Committee, Project T10/1562-D, Revision 2b, published 19 Oct. 2002, by American National Standards Institute (hereinafter termed the "SAS Standard") and/or later-published versions of the SAS Standard.

Depending upon, for example, whether bus 22 comprises a PCI Express™ bus or a PCI-X bus, circuit card slot 30 may comprise, for example, a PCI Express™ or PCI-X bus compatible or compliant expansion slot or interface 36. Interface 36 may comprise a bus connector 37 may be electrically and mechanically mated with a mating bus connector 34 that may be comprised in a bus expansion slot or interface 35 in circuit card 20.

Circuit card 20 may comprise an integrated circuit 40, operating mode selector circuitry 42, computer-readable boot code memory 39, and computer-readable memory 38. Alternatively, although not shown in the Figures, integrated circuit 40 may comprise memory 38 and/or memory 39. As used herein, an "integrated circuit" means a semiconductor device and/or microelectronic device, such as, for example, a semiconductor integrated circuit chip. Memories 38 and/or 39 each may comprise one or more of the following types of memories: semiconductor firmware memory, programmable memory, non-volatile memory, read only memory, electrically programmable memory, random access memory, flash memory, magnetic disk memory, and/or optical disk memory. Either additionally or alternatively, memories 38 and/or 39 each may comprise other and/or later-developed types of computer-readable memory.

Machine-readable firmware program instructions may be stored in memory 38. As described below, these instructions may be accessed and executed by integrated circuit 40. When executed by integrated circuit 40, these instructions may result in integrated circuit 40 performing the operations described herein as being performed by integrated circuit 40.

Slot 30 and card 20 are constructed to permit card 20 to be inserted into slot 30. When card 20 is properly inserted into slot 30, connectors 34 and 36 become electrically and mechanically coupled to each other. When connectors 34 and 36 are so coupled to each other, card 20 becomes electrically coupled to bus 22 and may exchange data and/or commands with system memory 21, host processor 12, and/or user interface system 16 via bus 22 and chipset 14.

Alternatively, without departing from this embodiment, the operative circuitry of card 20 may not be comprised in card 20, but instead, may be comprised in other structures, systems, and/or devices. These other structures, systems, and/or devices may be, for example, comprised in motherboard 32, coupled to bus 22, and exchange data and/or commands with other components (such as, for example, system memory 21, host processor 12, and/or user interface system 16) in system 100.

Figure 2:
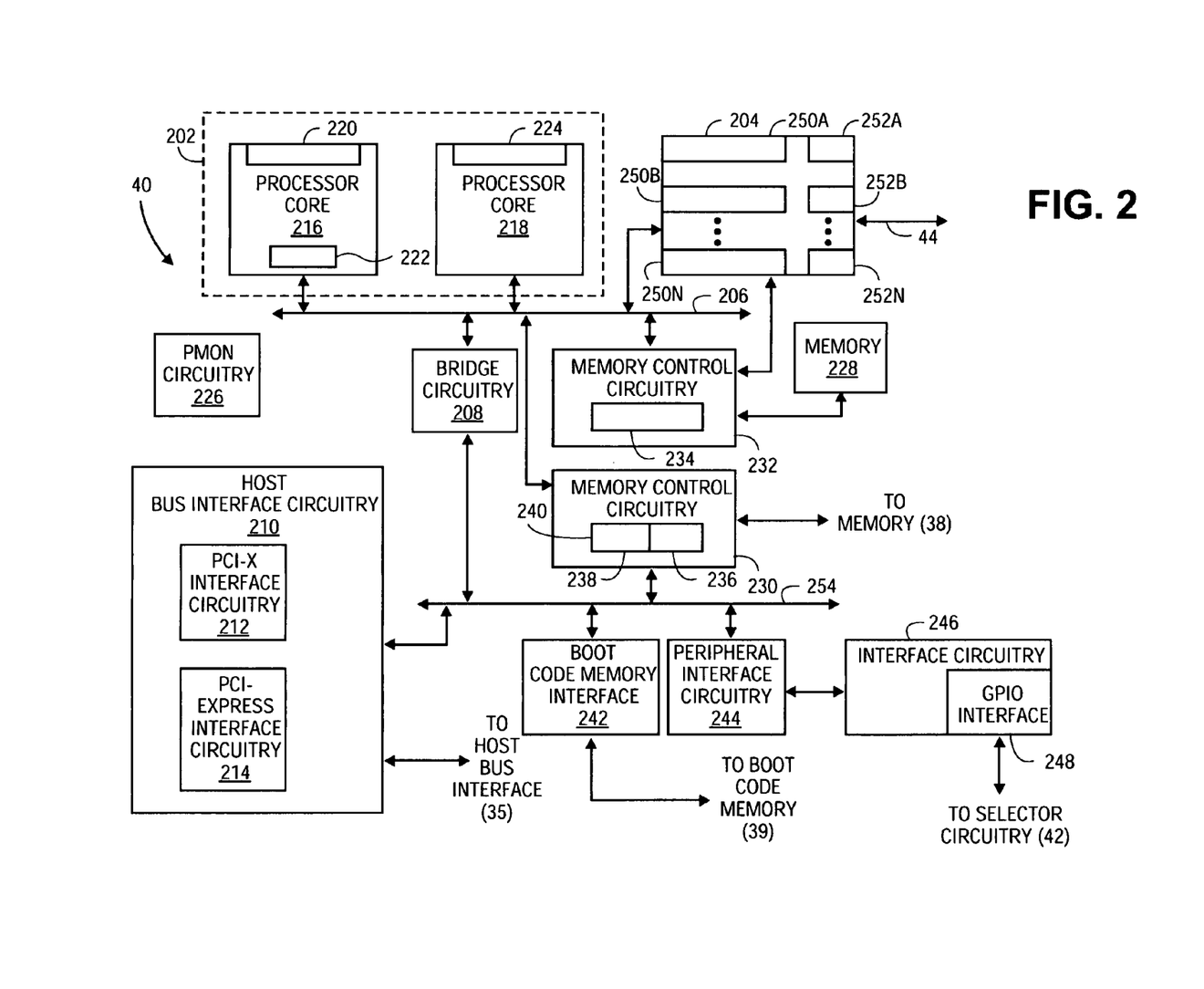
FIG. 2 is a diagram illustrating in greater detail an integrated circuit in the system embodiment of FIG. 1.

FIG. 2 is a diagram of integrated circuit 40. Integrated circuit 40 comprises processor circuitry 202, I/O interface circuitry 204, memory control circuitry 232, memory control circuitry 230, processor bus 206, and bus bridge circuitry 208. Processor circuitry 202, I/O interface circuitry 204, memory control circuitry 232, memory control circuitry 230, and bus bridge circuitry 208 may be electrically coupled to, and exchange data and/or commands via, bus 206. Bus bridge circuitry 208 may electrically couple processor bus 206 to input/output (I/O) bus 254, and may permit devices that may be coupled to bus 206 to exchange data and/or commands with devices that may be coupled to bus 254, while permitting the respective address spaces of buses 206 and 254 to be isolated from each other. Memory control circuitry 230, host bus interface circuitry 210, boot code memory interface 242, and peripheral interface circuitry 244 also may be electrically coupled to bus 254, and may exchange data and/or commands among each other via bus 254. Memory control circuitry 230 may be electrically coupled to memory 38. Boot code memory interface 242 may be coupled to memory 39. Memory control circuitry 232 may be electrically coupled to computer-readable memory 228. Memory 228 may comprise, for example, multi-port static random access memory (SRAM), although memory 228 may comprise other types of computer-readable memory without departing from this embodiment. Host bus interface circuitry 210 may be electrically coupled host bus interface 35.

Mode selector circuitry 42 may be electrically coupled to general purpose I/O interface circuitry 248 that may be comprised in interface circuitry 246. Interface circuitry 246 may comprise other and/or additional types of interface circuitry (not shown) without departing from this embodiment. The interface circuitry comprised in interface 246 may be coupled together via, for example, a peripheral bus (not shown) Interface 246 may be coupled to bus 254 via peripheral interface circuitry 244 that may permit the interface circuitry in circuitry 246 that may be coupled to the peripheral bus in circuitry 246 to exchange data and/or commands with devices that may be coupled to bus 254.

Boot code memory interface circuitry 242 may permit program instructions stored in memory 39 to be retrieved therefrom and executed by processor circuitry 202, after, for example, a reset of integrated circuit 40. More specifically, processor circuitry 202 may provide one or more commands to memory 39 and/or interface circuitry 242, via bus 206, bridge circuitry 208, bus 254, and interface circuitry 242, that may result such program instructions being retrieved from memory 39 and provided to circuitry 202, via interface 242, bus 254, bridge circuitry 208, and bus 206.

Integrated circuit 40 also may comprise performance monitoring (PMON) circuitry 226. PMON circuitry 226 may monitor, e.g., exchange of data and/or commands carried out via bus 206 and/or bus 254, and/or other and/or additional operations carried out by other circuitry in integrated circuit 40, and may determine, based at least in part upon such monitoring, whether integrated circuit 40 is operating properly. PMON circuitry 226 may indicate the results of its monitor activities to, e.g., processor circuitry 202 and/or external devices, such as, for example, host processor 12 via circuitry 210.

Processor circuitry 202 may include a plurality of processor cores 216 and 218. As used herein, a "processor core" may comprise hardwired circuitry, programmable circuitry, and/or state machine circuitry. Also, as used herein, "processor circuitry" may comprise hardwired circuitry, programmable circuitry, and/or state machine circuitry. In this embodiment, each processor core 216 and 218 may comprise respective circuitry that may be compatible and/or in compliance with the Intel® XScale™ Core micro-architecture described in Intel® XScale™ Core Developers Manual, published December 2000 by the Assignee of the subject application. Of course, as stated above, circuitry 202 may comprise other types of processor core circuitry without departing from this embodiment. In this embodiment, processor cores 216 and 218 may comprise, for example, computer-readable program instruction memory 220 and 224, respectively, that may contain respective sets of micro-code program instructions that processor cores 216 and 218, respectively, may execute. The execution of these respective sets of program instructions by processor cores 216 and 218, respectively, may result in, for example, the carrying out by circuitry 202, core 216, and/or core 218 of operations described herein as being carried out by circuitry 202, core 216, and/or core 218, respectively. At least a portion of these respective sets of program instructions may be retrieved from, e.g., boot code memory 39 after, for example, a reset of integrated circuit 40. Processor core 216 also may comprise a level-2 cache memory 222 that may be used by processor core 216 in carrying out the operations described herein as being carried out by processor core 216.

Interface circuitry 204 may comprise protocol engines 250A, 250B, ... 250N and physical layer interface circuitry 252A, 252B, ... 252N. As described below, each respective protocol engine 250A, 250B, ... 250N may be associated with, and exchange data and/or commands with respective physical layer interface circuitry 252A, 252B, ... 252N. Thus, for example, protocol engine 250A may be associated with, and exchange data and/or commands with physical layer interface circuitry 252A, protocol engine 250B may be associated with, and exchange data and/or commands with physical layer interface circuitry 252B, and protocol engine 250A may be associated with, and exchange data and/or commands with physical layer interface circuitry 252N, respectively. In this embodiment, the respective construction and operation of each of the protocol engines 250A, 250B, ... 250N may be respectively identical. Additionally, in this embodiment the respective construction and operation of each of the interfaces 252A, 252B, ... 252N may be respectively identical. Without departing from this embodiment, the respective numbers of protocol engines 252A, 252B, ... 252N, physical layer interfaces 252A, 252B, ... 252N, and links 44 may vary. However, in this embodiment, the number of protocol engines 250A, 250B, ... 250N may be equal to the number of physical layer interfaces 252A, 252B, ... 252N. In this embodiment, each of the physical layer interfaces 252A, 252B, ... 252N may be coupled to a respective one of the links 44; therefore, in this embodiment, the number of physical layers interfaces 252A, 252B, ... 252N may be equal to the number of links 44.

Host bus interface circuitry 210 may comprise respective interface circuitry that may be used to permit integrated circuit 40 to be able to exchange, in accordance with one of a plurality of different host bus protocols with which bus 22 may comply or be compatible, data and/or commands with other devices that may be coupled to bus 22. For example, in this embodiment, circuitry 210 may comprise PCI-X bus interface circuitry 212 and PCI Express™ bus interface circuitry 214. That is, as discussed below, depending, at least in part, upon the bus protocol with which bus 22 may comply or be compatible, a particular operating mode of integrated circuit 40 may be selected in which only a single appropriate one of the respective interface circuitry in circuitry 210 may be enabled to exchange data and/or commands with devices that may be coupled to bus 22, other respective interface circuitry in circuitry 210 may be disabled. For example, in this embodiment, if bus 22 is a PCI-X bus, then, in the selected operating mode, PCI-X interface circuitry 212 may be enabled and PCI Express™ bus interface circuitry 214 may be disabled. Conversely, in this embodiment, if bus 22 is a PCI-X bus, then, in the selected operating mode, PCI-X interface circuitry 212 may be disabled and PCI Express™ bus interface circuitry 214 may be enabled.

Although not shown in the Figures, in this embodiment, memory control circuitry 232 and/or DMA circuitry 234 may be electrically coupled to bus 254. In this embodiment, memory control circuitry 232 may comprise direct memory access (DMA) circuitry 234. Memory control circuitry 232 may control storage of data in, and retrieval of data from memory 228. For example, in this embodiment, memory control circuitry 232 may exchange commands and/or data with, for example, processor circuitry 202, interface circuitry 204, interface circuitry 210 and/or memory control circuitry 230. Based, at least in part, upon these commands, memory control circuitry 232 may exchange data and/or commands with memory 228. This may result in memory 228 storing and/or retrieving data in accordance with the commands and/or data supplied to memory controller circuitry 232. Additionally, depending upon the selected mode of operation of integrated circuit 40, DMA circuitry 234 may control, based upon commands and/or data received by circuitry 234 from other circuitry in integrated circuit 40, the exchange among I/O interface 204 and the other circuitry in integrated circuit 40 of data and/or commands received or intended to be transmitted by I/O interface circuitry 204 via one or more links 44. Without departing from this embodiment, DMA circuitry 234 may not be comprised in circuitry 232, but instead, may comprise circuitry that is distinct from circuitry 232, and is coupled to circuitry 232 and bus 254.

In this embodiment, memory control circuitry 230 may comprise RAID operation-related circuitry 240. Circuitry 240 may comprise, for example, DMA circuitry 238 and RAID calculation circuitry 236. Memory control circuitry 230 may control storage of data in, and retrieval of data from external memory 38. For example, in this embodiment, memory control circuitry 230 may exchange commands and/or data with, for example, processor circuitry 202, interface circuitry 210 and/or memory control circuitry 232. Based, at least in part, upon these commands, memory control circuitry 230 may exchange data and/or commands with memory 38. This may result in memory 38 storing and/or retrieving data in accordance with the commands and/or data supplied to memory controller circuitry 232. Additionally, depending upon the selected mode of operation of integrated circuit 40, DMA circuitry 238 may control, based upon commands and/or data received by circuitry 238 from other circuitry in integrated circuit 40, the exchange of RAID-related data among such other circuitry in integrated circuit 40. As used herein, "RAID-related data" means data involved in, generated as a result of, used as input or operands in, and/or used in carrying out and/or to facilitate operations involved in implementing and/or maintaining a RAID, such as, for example, RAID 29. RAID calculation circuitry 236 may comprise arithmetic accelerator circuitry (not shown) that may be capable of performing one or more arithmetic and/or logical operations using and/or involving RAID-related data, such as, for example, logical exclusive-or operations that may generate RAID parity data from initial user data and/or regenerate the initial user data from such RAID parity data. Without departing from this embodiment, DMA circuitry 238 and/or RAID calculation circuitry 236 may not be comprised in circuitry 230, but instead, may comprise circuitry that is distinct from circuitry 230, and is coupled to circuitry 230 and bus 254. Also without departing from this embodiment, integrated circuit 40 may not comprise RAID calculation circuitry 236, but alternatively, depending, at least in part, upon the selected operating mode of integrated circuit 40, the arithmetic and/or logical operations performed by circuitry 236 instead may be performed by processor core 216.

Figure 3:
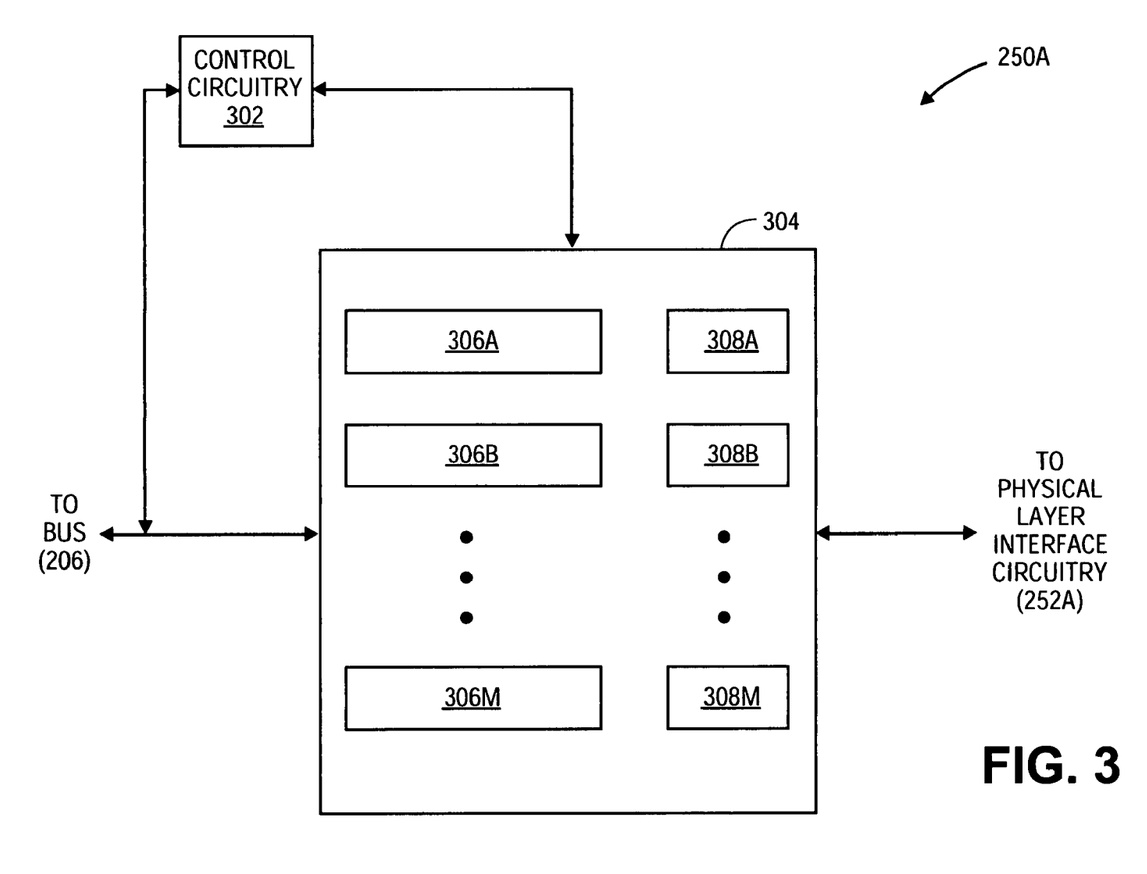
FIG. 3 is a diagram illustrating in greater detail interface circuitry in the integrated circuit of FIG. 2.

As stated previously, the respective construction of each of the protocol engines 250A, 250B, . . . 250N may be identical. FIG. 3 is a diagram that illustrates protocol engine 250A. Protocol engine 250A may comprise data transport layer protocol and data link layer protocol circuitry 304 and control circuitry 302. Data transport layer protocol and data link layer protocol circuitry 304 may be electrically coupled to control circuitry 302, bus 206, and physical layer interface circuitry 252A associated with protocol engine 250A. In this embodiment, circuitry 304 may include a plurality of different respective data transport layer protocol circuitry 306A, 306B, . . . 306M and a plurality of different respective data link layer protocol circuitry 308A, 308B, . . . 308M that may be respectively associated with the different respective data transport layer protocol circuitry 306A, 306B, . . . 306M. For example, in this embodiment, data transport layer protocol circuitry 306A may be associated with and electrically coupled to data link layer protocol circuitry 308A, data transport layer protocol circuitry 306B may be associated with and electrically coupled to data link layer protocol circuitry 308B, and data transport layer protocol circuitry 306M may be associated with and electrically coupled to data link layer protocol circuitry 308M, respectively.

In this embodiment, data transport layer protocol circuitry 306A, 306B, . . . 306M may be capable of carrying out different respective data transport layer communication protocols that may be associated with and/or comprised in the different respective communication protocols according to which card 20 may communicate with mass storage 28 via one or more links 44. Similarly, data link layer protocol circuitry 308A, 308B, . . . 308M may be capable of carrying out different respective link layer communication protocols that may be associated with and/or comprised in the different respective communication protocols according to which card 20 may communicate with mass storage 28 via one or more links 44. Each respective data transport layer protocol circuitry 306A, 306B, . . . 306M may be associated with and coupled to the respective link layer protocol circuitry 308A, 308B, . . . 308M that may be capable of carrying out the respective data link layer protocol that may be associated with and/or comprised in the same respective communication protocol as the respective data transport layer protocol that may be carried out that respective data transport layer protocol circuitry 306A, 306B, . . . 306M, respectively. For example, in this embodiment, circuitry 306A and circuitry 308A may be capable of carrying out a data transport layer protocol and a data link layer protocol, respectively, that may be associated with and/or comprised in the data transport layer protocol and data link layer protocol, respectively, used in an SAS protocol. Also for example, in this embodiment, circuitry 306B and circuitry 308B may be capable of carrying out a data transport layer protocol and a data link layer protocol, respectively, that may be associated with and/or comprised in the data transport layer protocol and data link layer protocol, respectively, used in an FC protocol. Additionally, for example, in this embodiment, circuitry 306M and 308M may be capable of carrying out a data transport layer protocol and a data link layer protocol, respectively, that may be associated with and/ or comprised in the data transport layer protocol and data link layer protocol, respectively, used in an S-ATA protocol. The number and types of different data transport layer and data link layer communication protocols that may be implemented by circuitry 304.

When active, each respective data transport layer protocol circuitry 306A, 306B, . . . 306M may be capable of providing control and/or data signals, in response, at least in part, to commands and/or data received from processor core 218 and in accordance with the respective data transport layer protocol carried out by the respective circuitry 306A, 306B, . . . 306M, to the respective data link layer circuitry 308A, 308B, . . . 308M with which the respective circuitry 306A, 306B, . . . 306M is associated. This may result in respective data link layer protocol circuitry 308A, 308B, . . . 308M that receives such control and/or data signals, providing corresponding control and/or data signals, in accordance with the respective data link layer protocol carried out by that respective data link layer circuitry, to physical layer interface circuitry 252A. This may result in physical layer interface circuitry 252A transmitting to mass storage 28, via one of the links 44, corresponding data and/or control signals, in accordance with the respective communication protocol (e.g., SAS, FC, or S-ATA) that comprises the respective data link layer protocol carried out by that respective data link layer circuitry.

Likewise, in this embodiment, physical layer interface circuitry 252A may receive data and/or control signals, in accordance with the respective communication protocol (e.g., SAS, FC, or S-ATA) utilized by the link in links 44 to which it is coupled, from mass storage 28. Depending at least in part upon the selected mode of operation of integrated circuit 40, physical layer interface circuitry 252A may provide the received data and/or control signals to data link layer protocol circuitry 308A, 308B, . . . 308M may be active in the selected mode of operation. This may result in the active data link layer protocol circuitry generating and supplying to the data transport layer protocol circuitry with which it is associated, in accordance with the respective data link layer protocol carried out by the active data link layer protocol circuitry, corresponding control and/or data signals for use by this data transport layer protocol circuitry. This may result in this transport layer protocol circuitry generating, in accordance with the data transport layer protocol carried out by this transport layer protocol circuitry, corresponding data and/or commands that may be intended for use, e.g., by an application program executed by processor circuitry 202 and/or host processor 12. Processor core 218 may signal memory control circuitry 232, interface circuitry 210, interface circuitry 204, and/or DMA circuitry 234. This may result in, for example, the data and/or commands generated by this transport layer protocol circuitry being stored in memory 228, provided to processor core 218, and/or provided to host processor 12 for use by, e.g., this application program.

In this embodiment, in response, at least in part to one or more commands received by interface circuitry 204 from, for example, processor core 218, control circuitry 302 in protocol engine 250A may select which of data transport layer protocol circuitry 306A, 306B, . . . 306M and which of data link layer protocol circuitry 308A, 308B, . . . 308M may be active and/or operational. That is, as discussed below, depending upon the selected mode of operation of integrated circuit 40, processor core 218 may provide to interface circuitry 204 one or more commands associated with this selected operating mode. This may result in control circuitry 302 signaling circuitry 304. This may result in only one of the transport layer protocol circuitry 306A, 306B, . . . 306M (e.g., circuitry 306A) and only one of the data link layer protocol circuitry 308A, 308B, . . . 308M (e.g., circuitry 308A associated with circuitry 306A) associated with the selected operating mode of integrated circuit 40 being active and/or operational in protocol engine 250A. As a result, protocol engine 250A may only communicate with mass storage 28 in accordance with the communication protocol (e.g., SAS protocol) that comprises and/or is associated with the transport and data link layer protocols carried out by the active transport and data link layer circuitry 306A and 308A, respectively, in protocol engine 250A. Thus, the selection of the mode of operation of integrated circuit 40 may correspond to and result in generation of one or more commands by processor core 218 that may result in the selection of which of the transport and data link layer protocol circuitry may be active and/or operational in protocol engine 250A, and thereby, the communication protocol that may be used by protocol engine 250A to communicate with mass storage 28. In a similar fashion, the one or more commands, provided by processor core 218 to interface circuitry 204 as a result of the selection of the mode of operation of integrated circuit 40, also may result the selection of respective communication protocols that may be used by each of the other protocol engines in interface circuitry 204 to communicate with mass storage 28. Additionally or alternatively, these one or more commands also may select which protocol engines 250A, 250B, . . . 250N may be enabled and/or operational, or disabled and/or non-operational.

In addition, depending at least in part upon the selected mode of operation of integrated circuit 40, processor core 216 and/or RAID operation-related circuitry 240 may be either enabled to perform or disabled from performing one or more operations involved in implementing and/or maintaining a RAID, such as, for example, RAID 29. For example, if processor core 216 and circuitry 240 are enabled to perform such operations, processor core 216 may execute, in response at least in part to, for example, one or more requests issued by host processor 12 to integrated circuit 40 to store, retrieve, and/or rebuild user data in RAID 29, program instructions stored in memory 220 that may result in processor core 216 determining in accordance, for example, with conventional RAID techniques, locations in RAID 29 in which to store and/or from which may be retrieved check data and/or user data associated with the check data. As used herein, "check data" means first data generated based at least in part upon second data and from which the second data may be regenerated at least in part. If the RAID level implemented in RAID 29 is equal to zero, the check data may be absent from RAID 29, and these locations may be comprise, for example, locations in RAID 29 of one or more stripes (not shown) of user data. If the RAID level implemented in RAID 29 is greater than one, the check data may comprise parity data and these locations may comprise, for example, locations in RAID 29 of one or more stripes (not shown) of such check data and/or user data. Alternatively, if the RAID level implemented in RAID 29 is equal to one (i.e., RAID 29 implements data mirroring), the check data may comprise a copy of the user data and these locations may comprise, for example, locations of the user data and the redundant copy of the user data in respective mirrored volumes (not shown) in RAID 29. In this embodiment, processor core 216 and/or RAID calculation circuitry 236 may utilize conventional RAID techniques to generate the check data based at least in part upon the user data and/or to regenerate the user data based at least in part upon the check data. Depending upon the selected operating mode of integrated circuit 40, processor core 218 may signal interface circuitry 204. This may result in one of the protocol engines (e.g., protocol engine 250A) transmitting to and/or retrieving from mass storage 28, via its associated interface 252A and one of the links 44 to which that interface 252A may be coupled, the user data and/or check data. The user data and/or check data may be stored in and/or retrieved from RAID at the locations determined by processor 216.

Figure 5:
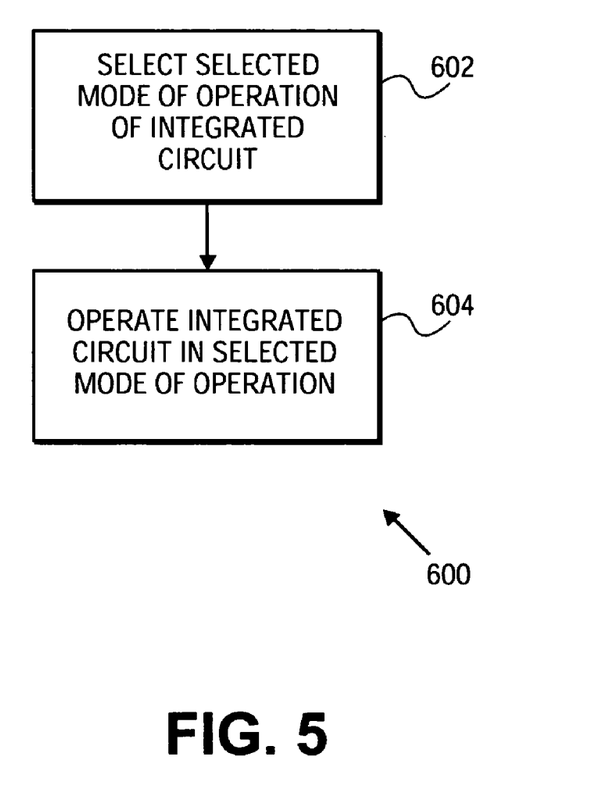
FIG. 5 is a flowchart illustrating operations that may be performed according to an embodiment.

Memory 39, memory 220, memory 224, and/or memory 228 may comprise program instructions that, when executed by integrated circuit 40, may result in, among other things, card 20 performing operations in accordance with one embodiment. FIG. 5 is a flowchart that illustrates these and other operations 600 that may be carried out in system 100, in accordance with one embodiment.

As illustrated by operation 602, operations 600 may commence with the selection of the selected mode of operation of integrated circuit 40. In this embodiment, the selected mode of operation of integrated circuit 40 may be selected, based upon and/or as a result, at least in part, of one or more signals provided to GPIO interface circuitry 248 from selector circuitry 42, one or more signals provided to host bus interface circuitry 210 by host processor 12, execution by processor circuitry 202 of one or more program instructions stored in memory 39, and/or detection and/or discovery by circuitry 204 of one or more respective communication protocols being used in one or more links 44.

For example, in this embodiment, selector circuitry 42 may comprise one or more jumpers and/or one or more dual in-line package (DIP) switches 43 that may be set (e.g., by a not shown human operator) in a plurality of different configurations to select the selected operating mode of integrated circuit 40. That is, the plurality of different configurations of the jumper and/or switches 43 may correspond to respective different operating modes of integrated circuit 40. When the one or more jumpers and/or one or more DIP switches 43 are set in a particular configuration, the selector circuitry 42 may generate one or more control signals that may correspond to and/or indicate the mode of operation of integrated circuit 40 that corresponds to that particular configuration. After, for example, a reset of integrated circuit 40, these one or more control signals may be supplied to processor cores 216 and 218 via circuitry 246, circuitry 244, bus 254, bridge circuitry 208, and bus 206.

In response, at least in part, to these one or more control signals, processor core 218 may generate and supply to interface circuitry 204 and/or host bus interface circuitry 210 one or more commands that may select, in accordance with the mode of operation of integrated circuit 40 that corresponds to and/or is indicated by the one or more control signals, which of bus interfaces 212 and 214 is to be enabled or disabled, respectively, which protocol engines 250A, 250B, . . . 250N are to be enabled or disabled, respectively, and/or the protocols that are to be implemented by protocol engines 250A, 250B, . . . 250N. Processor core 218 also may generate and supply to DMA circuitry 234 one or more commands that may either enable DMA circuitry 234 to control or disable DMA circuitry 234 from controlling, depending upon the mode of operation of integrated circuit 40 that corresponds to and/or is indicated by the one or more control signals, the exchange among I/O interface 204 and the other circuitry in integrated circuit 40 of data and/or commands received or intended to be transmitted by I/O interface circuitry 204 via one or more links 44.

Also in response, at least in part, to these one or more control signals from selector circuitry 42, processor core 216 may determine, in accordance with the mode of operation of integrated circuit 40 that corresponds to and/or is indicated by the one or more control signals, whether processor core 216 and/or RAID operation-related circuitry 240 are intended to be operative and/or enabled, or non-operative and/or disabled, given the operating mode of integrated circuit 40 selected by the jumpers and/or switches 43.

If processor core 216 determines that processor core 216 and/or RAID operation-related circuitry 240 are intended to be operative and/or enabled, processor core 216 may signal circuitry 240. This may result in processor core 216 and/or circuitry 240 performing one or more operations involved in implementing and/or maintaining a RAID, such as, for example, RAID 29.

Conversely, if processor core 216 determines that processor core 216 and/or RAID operation-related circuitry 240 are intended to be non-operative and/or disabled, processor core 216 may signal circuitry 240. This may result in processor core 216 and/or circuitry 240 being disabled from performing one or more operations involved in implementing and/or maintaining a RAID, such as, for example, RAID 29.

Alternatively or additionally, the one or more control signals from selector circuitry 42 also may be supplied to circuitry 210, circuitry 234, and/or circuitry 240. This may result in enabling or disabling of bus interface circuitry 212, bus interface circuitry 214, circuitry 240, and/or circuitry 234 in accordance with the mode of operation of integrated circuit 40 that corresponds to and/or is indicated by the one or more control signals.

Alternatively or additionally, in this embodiment, the selected mode of operation of integrated circuit 40 may be selected in operation 602, based upon and/or as a result, at least in part, of one or more signals provided to host bus interface circuitry 210 by host processor 12. For example, host bus interface circuitry 210 may include one or more memory locations (not shown) that may contain one or more values that may indicate the selected mode of operation of integrated circuit 40. These one or more memory locations may comprise, for example, one or more configuration registers. After a reset of system 100, these one or more values may indicate a default mode of operation of integrated circuit 40 in which an appropriate, predetermined one of interface circuitry 212 and interface circuitry 214 is enabled, depending upon whether, for example, bus 22 is a PCI-X bus or a PCI Express™ bus. Host processor 12 may initiate and/or execute one or more configuration cycles, in accordance with the bus protocol with which bus 22 may comply or be compatible, during which host processor 12 may provide one or more control signals to circuitry 210 that may result in a change, at least in part, of these one or more values to select the mode of operation in which integrated circuit 40 is desired to operate. That is, these one or more values, as changed, at least in part by host processor 12, may indicate a mode of operation in which integrated circuit 40 is desired to operate. Prior thereto or contemporaneously therewith, a human operator of system 100 may select the desired mode of operation of integrated circuit 40, and may issue one or more commands to host processor 12 via user interface system 16 that may result in host processor 12 changing these one or more values such that the one or more values, as changed, indicates this desired mode of operation.

Thereafter, processor cores 216 and 218 may examine these one or more values stored in the one or more memory locations in host bus interface circuitry 210, and may determine therefrom the selected mode of operation of integrated circuit 40. Processor core 218 may generate and supply to interface circuitry 204 one or more commands that may select, in accordance with the mode of operation of integrated circuit 40 that corresponds to and/or is indicated by these one or more values, which protocol engines 250A, 250B, . . . 250N are to be enabled or disabled, respectively, and/or the protocols that are to be implemented by protocol engines 250A, 250B, . . . 250N. Processor core 218 also may generate and supply to DMA circuitry 234 one or more commands that may either enable DMA circuitry 234 to control or disable DMA circuitry 234 from controlling, depending upon the mode of operation of integrated circuit 40 that corresponds to and/or is indicated by the one or more values, the exchange among I/O interface 204 and the other circuitry in integrated circuit 40 of data and/or commands received or intended to be transmitted by I/O interface circuitry 204 via one or more links 44.

Processor core 216 may determine, in accordance with the mode of operation of integrated circuit 40 that corresponds to and/or is indicated by the one or more values, whether processor core 216 and/or RAID operation-related circuitry 240 are intended to be operative and/or enabled, or non-operative and/or disabled, given the operating mode of integrated circuit 40 indicated by the one or more values.

If processor core 216 determines that processor core 216 and/or RAID operation-related circuitry 240 are intended to be operative and/or enabled, processor core 216 may signal circuitry 240. This may result in processor core 216 and/or circuitry 240 performing one or more operations involved in implementing and/or maintaining a RAID, such as, for example, RAID 29.

Conversely, if processor core 216 determines that processor core 216 and/or RAID operation-related circuitry 240 are intended to be non-operative and/or disabled, processor core 216 may signal circuitry 240. This may result in processor core 216 and/or circuitry 240 being disabled from performing one or more operations involved in implementing and/or maintaining a RAID, such as, for example, RAID 29.

Alternatively or additionally, circuitry 234 and/or circuitry 240 may examine the one or more values stored in circuitry 210. This may result in enabling or disabling of circuitry 240 and/or circuitry 234 in accordance with the mode of operation of integrated circuit 40 that corresponds to and/or is indicated by the one or more values.

Alternatively or additionally, in this embodiment, the selected mode of operation of integrated circuit 40 may be selected in operation 602, based upon and/or as a result, at least in part, of execution by processor circuitry 202 of one or more program instructions stored in memory 39. That is, according to this embodiment, different respective operating modes of integrated circuit 40 may be associated with different respective firmware program instruction set images that when executed, at least in part, by processor core 216 and processor core 218 may result in the respective operating modes being associated with these respective images being selected, and also may result in integrated circuit 40 operating in the respective operating modes. In this embodiment, only a single such firmware program instruction set image may be stored in memory 39, memory 220, and/or memory 224. This single firmware program instruction set image may comprise one or more firmware program instructions that may be executed by processor cores 216 and processor 218 after, for example, a reset of integrated circuit 40. This may result in processor core 218 generating and supplying to interface circuitry 204 one or more commands that may select, in accordance with the mode of operation of integrated circuit 40 that is associated with the single firmware program set image stored in memory 39, memory 220, and/or memory 224, which of interfaces 212 and 214 is to be enabled, and which protocol engines 250A, 250B, . . . 250N are to be enabled or disabled, respectively, and/or the protocols that are to be implemented by protocol engines 250A, 250B, . . . 250N. This may also result in processor core 218 generating and supplying to DMA circuitry 234 one or more commands that may either enable DMA circuitry 234 to control or disable DMA circuitry 234 from controlling, in accordance with the mode of operation of integrated circuit 40 that is associated with the single firmware program set image stored in memory 39, the exchange among I/O interface 204 and the other circuitry in integrated circuit 40 of data and/or commands received or intended to be transmitted by I/O interface circuitry 204 via one or more links 44.

The execution of these one or more program instructions by processor core 216 also may result in processor core 216 determining, in accordance with the mode of operation of integrated circuit 40 that is associated with this single firmware program instruction set image, whether processor core 216 and/or RAID operation-related circuitry 240 are intended to be operative and/or enabled, or non-operative and/or disabled, given this operating mode of integrated circuit 40.

If processor core 216 determines that processor core 216 and/or RAID operation-related circuitry 240 are intended to be operative and/or enabled, processor core 216 may signal circuitry 240. This may result in processor core 216 and/or circuitry 240 performing one or more operations involved in implementing and/or maintaining a RAID, such as, for example, RAID 29.

Conversely, if processor core 216 determines that processor core 216 and/or RAID operation-related circuitry 240 are intended to be non-operative and/or disabled, processor core 216 may signal circuitry 240. This may result in processor core 216 and/or circuitry 240 being disabled from performing one or more operations involved in implementing and/or maintaining a RAID, such as, for example, RAID 29.

Alternatively or additionally, in this embodiment, the selected mode of operation of integrated circuit 40 may be selected in operation 602, based upon and/or as a result, at least in part, of detection and/or discovery by circuitry 204 of the one or more respective communication protocols being used by one or more links 44. That is, circuitry 204 may examine signals transmitted to circuitry 204 via one or more links 44 that may embody data and/or commands, and may detect and/or discover, based at least in part upon such examination, one or more respective communication protocols via which such commands and/or data may have been transmitted to circuitry 204 via one or more links 44. Circuitry 204 may provide one or more signals to processor core 218 that may indicate these one or more detected and/or discovered protocols, and may select, in accordance with these detected and/or discovered protocols, which protocol engines 250A, 250B, . . . 250N are to be enabled or disabled, respectively, and/or the one or more protocols that are to be implemented by protocol engines 250A, 250B, . . . 250N. Based at least in part upon the indication provided to processor core 218 by circuitry 204, processor core 218 may generate and supply to DMA circuitry 234 one or more commands that may enable DMA circuitry 234 to control the exchange among I/O interface 204 and the other circuitry in integrated circuit 40 of data and/or commands received or intended to be transmitted by I/O interface circuitry 204 via one or more links 44. One or more signals provided to GPIO interface circuitry 248 from selector circuitry 42, one or more signals provided to host bus interface circuitry 210 by host processor 12, and/or execution by processor circuitry 202 of one or more program instructions stored in memory 39 may be used to select, for example, in the manner described previously, whether processor core 216 and/or RAID operation-related circuitry 240 are intended to be operative and/or enabled, or non-operative and/or disabled, and which of interfaces 212 and 214 is to be enabled.

After the selected mode of operation of integrated circuit 40 has been selected as a result of operation 602, integrated circuit 40 may operate in the selected mode of operation, as illustrated by operation 604 in FIG. 5. For example, one operating mode that may be selected as a result of operation 602 may be carried out by integrated circuit 40 in system 100' shown in FIG. 4. Unless stated to contrary, the construction and operation of system 100' may be substantially identical to the construction and operation of system 100 shown in FIG. 1. In this one mode of operation of integrated circuit 40, interface circuitry 204 may exchange data and/or commands with RAID 29, based at least in part, upon commands received from processor core 218. Processor core 216 and circuitry 240 may be disabled, and one or more operations comprised in carrying out and/or facilitating operations involved in implementing and/or maintaining RAID 29 may be executed by a RAID controller card 504, instead of by processor core 216 and/or circuitry 240. In system 100', card 504 may comprise a bus interface 510. Depending upon, for example, whether bus 22 comprises a PCI Express™ bus or a PCI-X bus, system 100' may comprise a circuit card slot 502 that may include a circuit card slot 510 that may comprise, for example, a PCI Express™ or PCI-X bus compatible or compliant expansion slot or interface 506. Interface 506 may comprise a bus connector 508 may be electrically and mechanically mated with a mating bus connector 512 that may be comprised in a bus expansion interface 510 in circuit card 504. When connector 508 is mated with connector 512, card 504 may exchange data and/or commands with other devices, such as, for example, card 20 via bus 22.

Figure 4:
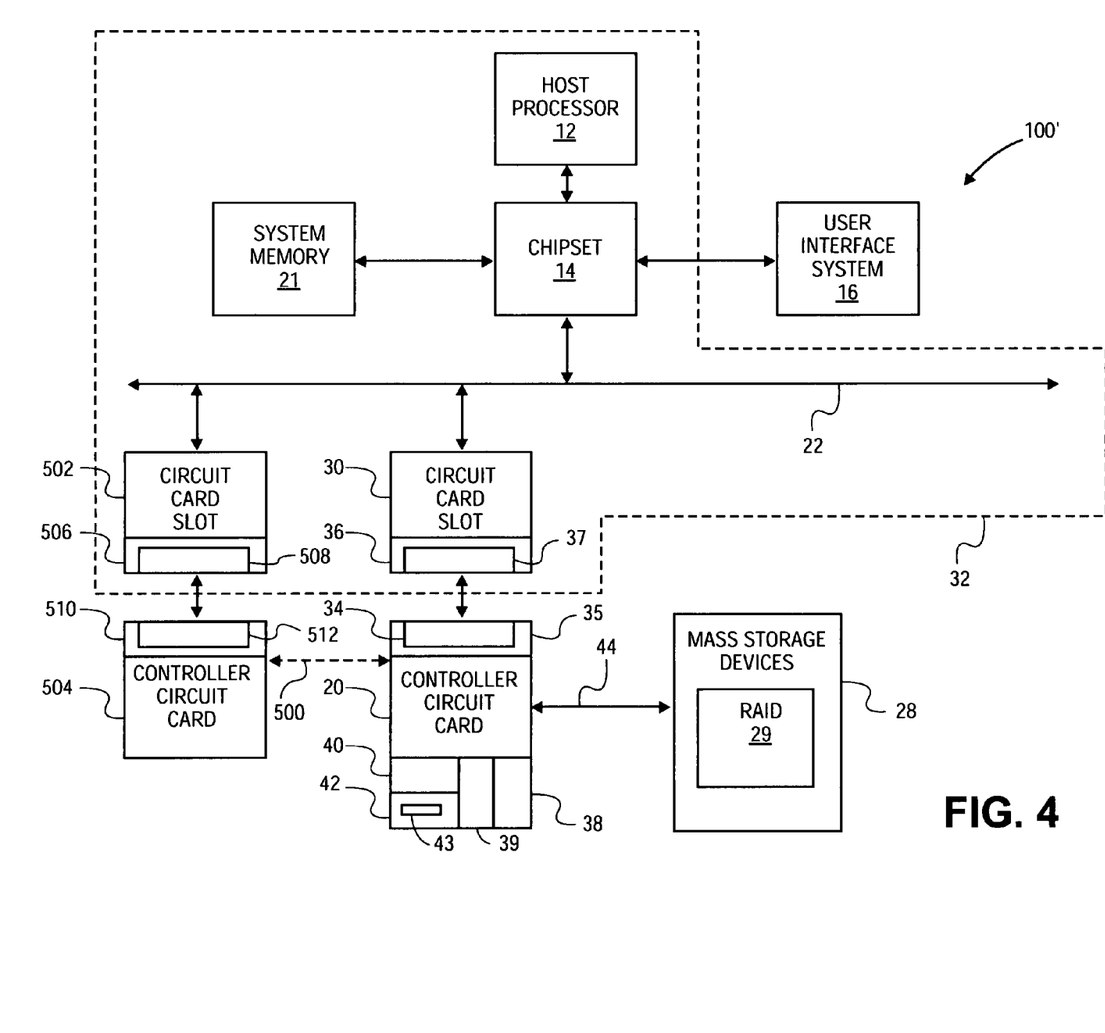
FIG. 4 is a diagram illustrating another system embodiment.

In system 100', data and/or commands received by card 20 from RAID 29 that are intended to undergo and/or to be used in one or more one or more operations comprised in carrying out and/or facilitating operations involved in implementing and/or maintaining RAID 29 may be transmitted from integrated circuit 40 via bus 22 to card 504. Card 504 may carry out such operations and transmit to integrated circuit 40 other commands and/or data that may represent and/or embody the results of such operations. Processor core 218 may provide one or more control signals to interface 204 that may result in interface 204 transmitting these other data and/or commands to RAID 29 to implement and/or maintain, at least in part, RAID 29.

Alternatively, in another mode of operation of integrated circuit 40, instead of and/or in addition to exchanging data and/or commands with integrated circuit 40 via bus 22, card 504 may exchange data and/or commands with integrated circuit 40 via one or more communication links 500 that may be coupled to one or more respective physical interfaces 252A, 252B, . . . 252N. That is, in this other mode of operation of integrated circuit 40, a subset of physical interfaces 252A, 252B, . . . 252N may be coupled to one or more links 44, and a different subset of physical interfaces 252A, 252B, . . . 252N may be coupled to card 504 via one or more links 500. In this other mode of operation of integrated circuit 40, processor core 216 and circuitry 240 may be disabled, and data and/or commands received by card 20 from RAID 29 that are intended to undergo and/or to be used in one or more operations comprised in carrying out and/or facilitating operations involved in implementing and/or maintaining RAID 29 may be transmitted from integrated circuit 40 via one or more links 500 to card 504. Card 504 may carry out such operations and transmit to integrated circuit 40 other commands and/or data that may represent and/or embody the results of such operations. Processor core 218 may provide one or more control signals to interface 204 that may result in interface 204 transmitting these other data and/or commands to RAID 29 to implement and/or maintain, at least in part, RAID 29.

Thus, in summary, one system embodiment may comprise a circuit card capable of being coupled to storage. The circuit card may include an integrated circuit. The integrated circuit may be capable of operating in a selected mode of operation. The integrated circuit may comprise first circuitry and second circuitry. The first circuitry may be capable of performing at least one operation that comprises, at least in part, generating check data based at least in part upon other data, regenerating the other data based at least in part upon the check data, and/or determining locations of the check data and the other data in the storage. The second circuitry may be capable of controlling, at least in part, at least one interface to transmit from and/or receive at the integrated circuit the check data and/or the other data. Depending at least in part upon the selected mode of operation of the integrated circuit, the first circuitry may be enabled to perform or disabled from performing the at least one operation.

Also in summary, one system embodiment may comprise a circuit card that includes an integrated circuit. The circuit card may be capable of being coupled to a bus. The integrated circuit may be capable of operating in a selected mode of operation. The integrated circuit may comprise processor circuitry and interface circuitry. The processor circuitry may include a plurality of processor cores. The interface circuitry may be capable of communicating in accordance a plurality of different protocols. At least one of the processor cores may be capable of issuing a command to the interface circuitry to communicate in accordance with at least one of the plurality of different protocols that corresponds to the selected mode of operation of the integrated circuit.

Advantageously, the integrated circuits of these system embodiments may offer enhanced communication capabilities, and may communicate using a greater number of host bus and communication protocols, compared to the prior art. Also advantageously, the host bus and/or communication protocols used by these integrated circuits of these system embodiments may be selected. Additionally, the integrated circuits of these system embodiments may include single respective packages and/or "foot prints" that may include circuitry that may be used to perform RAID-related operations and/or communication protocol operations. Advantageously, this may improve the utility and/or versatility of the integrated circuits of these system embodiments, since these integrated circuits may be used to perform such RAID-related operations or may be used together with other RAID controller devices that may perform such operations.

The terms and expressions which have been employed herein are used as terms of description and not of limitation, and there is no intention, in the use of such terms and expressions, of excluding any equivalents of the features shown and described (or portions thereof), and it is recognized that various modifications are possible within the scope of the claims. Accordingly, the claims are intended to cover all such equivalents.

What is claimed is:

1. A method comprising:
   selecting one of a plurality of modes of operation of a single integrated circuit coupled between a host bus and a set of one or more storage devices; and
   based on the selected mode of operation, enabling at least one of a plurality of storage protocols for communicating with the set of one or more storage devices, and one or more operations for maintaining a Redundant Array of Inexpensive Disks (RAID) system that includes the set of one or more storage devices.

2. The method of claim 1, further comprising:
   one of enabling and disabling one of a plurality of host bus protocols based on the selected one of the plurality of modes of operation.

3. The method of claim 1, further comprising:
   one of enabling and disabling a Direct Memory Access (DMA) operation based on the selected one of the plurality of modes of operation, wherein the DMA operation includes controlling an exchange of commands and data.

4. The method of claim 1, wherein the selecting comprises:
   storing one or more program instructions, wherein the one or more program instructions are associated with one of the plurality of modes of operation;
   executing the one or more program instructions.

5. The method of claim 1, wherein the selecting comprises:
   detecting one or more storage protocols used by the set of storage devices.

6. The method of claim 1, wherein the selecting comprises:
   reading an input device to detect which of a plurality of different configurations is currently selected, wherein each of the plurality of configurations corresponds to one of the plurality of modes of operation of the single integrated circuit.

7. The method of claim 1, further comprising:
   storing one or more values that indicate a first of the plurality of modes of operation;
   selecting a second of the plurality of modes of operation by changing the one or more values;
   examining the changed one or more values; and
   implementing the second of the plurality of modes of operation based on the examination.

8. A machine-readable medium containing instructions which, when executed by a processing system, cause the processing system to perform operations, the operations comprising:
   selecting one of a plurality of modes of operation of a single integrated circuit coupled between a host bus and a set of one or more storage devices; and
   based on the selected mode of operation, enabling at least one of,
   one of a plurality of storage protocols for communicating with the set of one or more storage devices, and
   one or more operations for maintaining a RAID system that includes the set of one or more storage devices.

9. The machine readable medium of claim 8, further comprising:
   one of enabling and disabling one of a plurality of host bus protocols based on the selected one of the plurality of modes of operation.

10. The machine readable medium of claim 8, wherein the selecting comprises:
    detecting one or more storage protocols used by the set of storage devices.

11. An apparatus comprising:
    a single integrated circuit to be coupled between a host bus and a set of one or more storage devices and configurable for a plurality of modes of operation, the single integrated circuit including,
    processor circuitry coupled with an internal bus circuitry and configured to generate at least one mode selection command corresponding to a currently selected one of the plurality of modes of operation of the integrated circuit,
    host bus interface circuitry to be coupled with the host bus and coupled with the internal bus circuitry, and configured to receive the at least one mode selection command via the internal bus circuitry, the host bus interface circuitry capable of communicating using a plurality of host bus protocols and configured to communicate using one of the plurality of host bus protocol depending on the currently selected one of the plurality of modes of operation, Input/Output (I/O) interface circuitry to be coupled with the set of storage devices and coupled with the internal bus circuitry, and configured to receive the at least one mode selection command via the bus circuitry, the I/O interface circuitry capable of communicating using a plurality of storage protocols and configured to communicate using one of the plurality of storage protocols depending on the currently selected one of the plurality of modes of operation, and RAID operation related circuitry coupled with the internal bus circuitry and configured to receive the mode selection command from the processor circuitry, and to be one of enabled to perform and disabled from performing one or more operations involved in implementing a RAID, depending on the currently selected one of the plurality of modes of operation.

12. The apparatus of claim 11, wherein:
the processor circuitry includes a first processor core and a second processor core, the first processor core to deliver a first mode selection command to the host bus circuitry and a second mode selection command to the I/O interface circuitry, and the second processor core to deliver a third mode selection command to the RAID operation related circuitry.

13. The apparatus of claim 12, further comprising:
an external selector circuitry coupled to the integrated circuit via the GPIO interface, wherein the control signal is based on a physical configuration of at least one of a jumper and a dual in-line package (DIP) switch.

14. The apparatus of claim 11, wherein:
the host bus circuitry includes a first circuitry and a second circuitry;
the first circuitry to implement communication over the host bus using Peripheral Component Interconnect (PCI) Express;
the second circuitry to implement communication over the host bus using PCI-X.

15. The apparatus of claim 11, wherein:
the I/O interface circuitry includes a plurality of protocol engines and respective physical layer interface circuitry to implement each of the plurality of storage protocols, wherein each protocol engine can communicate via the respective physical layer circuitry in accordance with the plurality of different protocols.

16. The apparatus of claim 15, wherein:
the one or more values stored within the memory include a program instruction set associated with one of the plurality of modes of operation; and
the processor circuitry is configured to execute the program instruction set stored within the memory and to generate the mode selection command based on the execution.

17. The apparatus of claim 11, wherein:
the plurality of storage protocols include at least two of Serial Small Computer Interface (SAS), Serial Advanced Technology Attachment (SATA), and Fibre Channel (FC).

18. The apparatus of claim 11, wherein the single integrated circuit further comprises:
a General Purpose Input Output (GPIO) interface configured to receive a control signal originating externally to the integrated circuit;
a peripheral interface circuitry to communicatively couple the GPIO interface with the internal bus circuitry; and
wherein
the processor circuitry is configured to generate the mode selection command in response to the control signal received via the GPIO interface.

19. The apparatus of claim 11, wherein:
the integrated circuit includes a memory to store one or more values, the one or more values used to determine the currently selected one of the plurality of modes of operation of the integrated circuit; and
the processor circuitry is configured to access the memory via the bus circuitry to determine the one or more values and to generate the mode selection command based on the one or more values.

20. The apparatus of claim 11, wherein:
the I/O interface circuitry is configured to detect each of the plurality of storage protocols received from the set of one or more storage devices with which the I/O interface circuitry is capable of communicating and to indicate a detected storage protocol to the processor circuitry; and
the processor circuitry is configured to receive the indication via the internal bus circuitry and to generate the mode selection command based on the detected storage protocol.

21. A system comprising:
a storage bus to couple a single integrated circuit with a set of one or more storage devices, wherein the storage bus includes a cable configured to implement communication with SAS and SATA devices; and
the single integrated circuit to be coupled between a host bus and the set of one or more storage devices and configurable for a plurality of modes of operation, the single integrated circuit including,
processor circuitry coupled with an internal bus circuitry and configured to generate at least one mode selection command corresponding to a currently selected one of the plurality of modes of operation of the integrated circuit,
host bus interface circuitry to be coupled with the host bus and coupled with the internal bus circuitry, and configured to receive the at least one mode selection command via the internal bus circuitry, the host bus interface circuitry capable of communicating using a plurality of host bus protocols and configured to communicate using one of the plurality of host bus protocol depending on the currently selected one of the plurality of modes of operation,
I/O interface circuitry to be coupled with the set of storage devices and coupled with the internal bus circuitry, and configured to receive the at least one mode selection command via the bus circuitry, the I/O interface circuitry capable of communicating using a plurality of storage protocols and configured to communicate using one of the plurality of storage protocols depending on the currently selected one of the plurality of modes of operation, and
RAID operation related circuitry coupled with the internal bus circuitry and configured to receive the mode selection command from the processor circuitry, and to be one of enabled to perform and disabled from performing one or more operations involved in implementing a RAID, depending on the currently selected one of the plurality of modes of operation.

22. The system of claim 21, wherein:
the processor circuitry includes a first processor core and a second processor core, the first processor core to deliver a first mode selection command to the host bus circuitry and a second mode selection command to the I/O interface circuitry, and the second processor core to deliver a third mode selection command to the RAID operation related circuitry.

23. The system of claim 21, wherein:
the host bus circuitry includes a first circuitry and a second circuitry;
the first circuitry to implement communication over the host bus using PCI Express;
the second circuitry to implement communication over the host bus using PCI-X.

24. The system of claim 21, wherein:
the I/O interface circuitry includes a plurality of protocol engines and respective physical layer interface circuitry to implement each of the plurality of storage protocols, wherein each protocol engine can communicate via the respective physical layer circuitry in accordance with the plurality of different protocols.

25. The system of claim 21, wherein:
the plurality of storage protocols include at least two of SAS, SATA, and FC.

26. The system of claim 21, wherein:
the I/O interface circuitry is configured to detect each of the plurality of storage protocols received from the set of one or more storage devices with which the I/O interface circuitry is capable of communicating and to indicate a detected storage protocol to the processor circuitry; and
the processor circuitry is configured to receive the indication via the internal bus circuitry and to generate the mode selection command based on the detected storage protocol.

* * * * *

UNITED STATES PATENT AND TRADEMARK OFFICE
CERTIFICATE OF CORRECTION

PATENT NO. : 7,640,481 B2
APPLICATION NO. : 11/389340
DATED : December 29, 2009
INVENTOR(S) : Beckett et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 810 days.

Signed and Sealed this

Ninth Day of November, 2010

David J. Kappos
*Director of the United States Patent and Trademark Office*